US008794081B2

(12) United States Patent
Haartsen et al.

(10) Patent No.: US 8,794,081 B2
(45) Date of Patent: Aug. 5, 2014

(54) SENSOR FOR DETECTING BUBBLES IN A LIQUID FLOWING THROUGH A FLOW PATH

(75) Inventors: Jaap Roger Haartsen, Eindhoven (NL); Ronald Dekker, Eindhoven (NL)

(73) Assignee: Koninklijke Philips N.V., Eindhoven (NL)

( * ) Notice: Subject to any disclaimer, the term of this patent is extended or adjusted under 35 U.S.C. 154(b) by 417 days.

(21) Appl. No.: 13/203,801

(22) PCT Filed: Mar. 3, 2010

(86) PCT No.: PCT/IB2010/050910
§ 371 (c)(1),
(2), (4) Date: Aug. 29, 2011

(87) PCT Pub. No.: WO2010/100611
PCT Pub. Date: Sep. 10, 2010

(65) Prior Publication Data
US 2011/0308328 A1    Dec. 22, 2011

(30) Foreign Application Priority Data

Mar. 5, 2009  (EP) .................................... 09154369

(51) Int. Cl.
*G01F 13/00* (2006.01)
*G01F 1/68* (2006.01)

(52) U.S. Cl.
USPC .................................... 73/861.41; 73/204.11

(58) Field of Classification Search
CPC ............. A61B 18/148; A61B 18/1482; A61B 2018/00083; A61B 2018/00196; A61B 2018/00434; A61B 2018/0044; A61B 2018/1475; A61B 2018/1497; A61B 18/1233; A61B 18/14; A61B 2018/00029; A61B 2018/00702
See application file for complete search history.

(56) References Cited

U.S. PATENT DOCUMENTS

| 4,384,578 A | 5/1983 | Winkler |
| 4,555,940 A | 12/1985 | Renger |
| 5,072,235 A | 12/1991 | Slowik |
| 7,927,302 B2 * | 4/2011 | Arnold et al. ................. 604/113 |
| 2007/0078610 A1 | 4/2007 | Adams et al. |
| 2011/0118705 A1 * | 5/2011 | Dekker et al. ............. 604/890.1 |

FOREIGN PATENT DOCUMENTS

| DE | 4142838 A1 | 7/1992 |
| DE | 19725977 A1 | 12/1998 |
| DE | 102008011117 A1 | 8/2009 |
| EP | 0405148 A1 | 5/1990 |
| JP | 2009276323 A | 11/2009 |

* cited by examiner

Primary Examiner — Harshed R Patel

(57) ABSTRACT

A sensor for detecting bubbles in gas phase present in a liquid flowing through a flow path. The sensor can include a heating element for heating the liquid, which can be provided with a predetermined level of power at least during detecting, and a transducer arrangement arranged for generating a measurement signal indicative for the temperature of the heating element. The sensor furthermore can include a comparator arrangement for comparing a measurement value of the measurement signal with a predetermined threshold level, which can correspond to a reference temperature attainable by the heating element in response to the predetermined level of power and a minimum velocity attainable by the liquid in the flow path. Based on the latter comparison, the comparator arrangement can generate an output signal indicative for a possible presence of bubbles in gas phase.

14 Claims, 3 Drawing Sheets

SENSOR FOR DETECTING BUBBLES IN A LIQUID FLOWING THROUGH A FLOW PATH

FIELD OF THE INVENTION

The invention relates to a sensor for detecting bubbles in gas phase present in a liquid flowing through a flow path.

The invention further relates to a control unit for cooperation with the sensor.

The invention further relates to a system comprising the sensor and the control unit.

BACKGROUND OF THE INVENTION

In U.S. Pat. No. 4,555,940, an apparatus for measuring and for monitoring the volume and rate of liquid flow through a flow path is disclosed. The apparatus disclosed in U.S. Pat. No. 4,555,940 includes a means for modifying the temperature of a part of the liquid flow path. After a fixed amount of heat is delivered, and the temperatures of the liquid flow path and the liquid therein have been sufficiently modified, a temperature change detector means is activated. Said detector means monitors changes in temperature as a function of liquid flow rates through a temperature modified portion of the liquid flow path. The apparatus according to U.S. Pat. No. 4,555,940 can detect bubbles by employing the fact that the temperature of the temperature modified portion of the liquid flow path will increase when bubbles pass through compared to temperature when only liquid is flowing through said temperature modified portion, provided the amount of heat transferred to the temperature modified portion of the liquid flow path remains substantially unchanged.

The techniques disclosed in U.S. Pat. No. 4,555,940 are not capable of detecting the presence of bubbles in gas phase when alterations of liquid flow velocity are conceivable. Namely, the techniques disclosed in U.S. Pat. No. 4,555,940 cannot discriminate between the various causes of temperature changes of either the liquid flow path or the liquid therein. That is, provided the amount of heat transferred to the temperature modified portion of the liquid flow path remains substantially unchanged, a temperature change is attributable to a change in liquid flow rate as well as a presence of bubbles. As a result, no appropriate action can be deployed based on the registered temperature change.

SUMMARY OF THE INVENTION

It is an object of the invention to provide a sensor capable of detecting bubbles in gas phase present in a liquid flowing through a flow path, which detecting is robust regarding a change in velocity of said liquid flowing through the flow path.

The sensor according to the invention comprises a heating element for heating the liquid, which heating element is provided with a predetermined level of power at least during detecting, the sensor furthermore comprises a transducer arrangement arranged for generating a measurement signal representing a measurement value indicative for the temperature of the heating element, and a comparator arrangement for comparing the measurement value of the measurement signal with a predetermined threshold level. Herein the predetermined threshold level corresponds to a reference temperature attainable by the heating element in response to said predetermined level of power and to a minimum velocity attainable by the liquid in the flow path. The comparator arrangement is furthermore configured for generating an output signal when the measurement value of the measurement signal exceeds the predetermined threshold level.

Through basing the output signal on a comparison of the measurement value represented by the measurement signal with the predetermined threshold level, wherein said predetermined threshold level corresponds to the reference temperature attainable by the heating element in response to said predetermined level of power and to a minimum velocity attainable by the liquid in the flow path, the detecting of gas bubbles is robust regarding presumable alterations of the velocity of the liquid flowing through the flow path. Namely, on the condition that the power supplied to said heating element is preserved at the predetermined level, the temperature of the heating element increases with decreasing velocity of the liquid flowing through the flow path. Nonetheless, the heating element's temperature will not exceed the reference temperature attainable by the heating element in response to said predetermined level of power and a minimum velocity. By selecting the predetermined threshold such that it corresponds to said reference temperature, and by employing the characteristic that the fluid has a thermal conductivity that exceeds a bubbles' thermal conductivity, a conceivable exceeding of the predetermined threshold level by the heating element's temperature is merely attributable to the presence of bubbles in gas phase in the liquid flowing through the flow path. As a result, the sensor according to the invention allows for an accurate detecting of a possible presence of bubbles in gas phase in the liquid flowing through the flow path. Consequently, for medical applications such as intravenous infusion, anesthesia flow control and urinary catheters, the supply of a harmful amount e.g. air bubbles to a patient is effectively prevented from. In this text, a liquid's thermal diffusivity is defined as the ratio of a liquid's thermal conductance to said liquid's volumetric heat capacity. An equivalent definition is employed for the bubbles' thermal diffusivity.

In a further preferred embodiment of the sensor according to the invention, the transducer arrangement is arranged for generating a further measurement signal representing a further measurement value indicative for the velocity of the liquid flowing through the flow path. This embodiment is beneficial, especially for medical interventions such as intravenous infusion, anesthesia flow control and urinary catheters, in the sense that it provides information regarding a rate at which e.g. medication is being supplied or information concerning a cumulative amount of medication supplied to the patient.

In a preferred embodiment of the sensor according to the invention, the output signal is indicative for a duration of the time during which the measurement value of the measurement signal exceeds the predetermined threshold. This embodiment has the advantage that it provides a measure for the amount of bubbles in gas phase present in the liquid flowing through the flow path having passed the transducer arrangement. Namely, by monitoring the further measurement value indicative for the velocity at which the liquid is flowing through the flow path in combination with the duration of the time during which the measurement value of the measurement signal exceeds the predetermined threshold, an estimation of the amount of bubbles that has passed the transducer arrangement is obtained. For instance, when being applied in intravenous drug supply systems, dedicated actions may be deployed following upon the measurement signal indicates a critical amount of e.g. air, which air is conceivably present in a liquid medication to be intravenously supplied to a patient, has been transported through the flow path to said patient. Through establishing said critical level of e.g. air, superfluous notifying of the medical professional is prevented from.

In a further preferred embodiment of the sensor according to the invention, the further measurement value represented by the measurement signal is based on a ratio of a first spatial temperature difference and a second spatial temperature difference. This embodiment has the advantage that an accuracy of the further measurement signal is significantly increased. Namely, through basing the measurement signal on a ratio of a first spatial temperature difference and a second spatial temperature difference, the measurement signal is robust regarding an actual level of power supplied to the heating element. Hence, regardless of the predetermined level of power supplied to the heating element at least during detecting a possible presence of bubbles in gas phase in the liquid, the accuracy of the further measurement signal is preserved. Herein, a spatial temperature difference implies the numerical difference between temperatures measured at distinct locations along the flow path. The first spatial temperature difference and the second temperature difference both relate to the power dissipated by the heating element in an affine way, at least for a range of liquid flow velocities. An affine relation amounts to a linear relation provided the constant term of the linear expression equals zero. Therefore, by taking the ratio the first spatial temperature difference and the second temperature difference, a relation is obtained which is independent of the power dissipated by the heating element.

In a further preferred embodiment of the sensor according to the invention, the sensor comprises a sensor receiver arranged for receiving an electromagnetic radiation and for powering the heating element following upon receiving the electromagnetic radiation. This embodiment has the advantage that the heating element may be powered wirelessly, i.e. the electromagnetic radiation may be provided in a wireless manner. The latter feature enables an easy handling for the sensor due to the absence of bothersome wiring. Herein the heating element can be powered via the energy contained in the electromagnetic radiation itself. Alternatively, the electromagnetic radiation can be employed to enable an energy storage comprised in the sensor such as a miniaturized battery, which miniaturized battery powers the heating element in its turn.

In a further preferred embodiment of the sensor according to the invention, the sensor comprises a sensor transmitter for transmitting the output signal generated by the comparator arrangement and/or the further measurement signal generated by the transducer arrangement to a control receiver comprised in the control unit. This embodiment has the advantage that the sensor is physically disconnected from any circuitry that drives the sensor and that responds to the output signal and/or the further measurement signal. As a result, this embodiment allows for a reliable handling and a reliable application since the risk of pollution of electrical contacts, which is inherently present in e.g. medical applications, is rather limited through providing a wireless transmitting of the output signal and/or the further measurement signal. The latter quality guarantees an economically attractive employment in applications in which the channel is regularly replaced. Namely, the sensor is easily disconnectable from the control unit due to the absence of bothersome wiring. After disconnection, the control unit can be reused whereas the sensor allows for disposal. Particularly in applications in which the channel is regularly replaced, such as intravenous infusion, anesthesia flow control, urinary catheters, breathing control as well as enteral and parenteral nutrition flow measurement, the latter quality is very beneficial. Because of the sensor's disposability, the extremely labor-intensive process of making the sensor sterile again is effectively circumvented. Obviously, the sensor need not necessarily be disposed, i.e. it clearly does allow for a prolonged use.

In a further preferred embodiment of the sensor according to the invention, the sensor receiver is an antenna, which antenna comprises the heating element. This embodiment has the advantage that no rectifier and no accompanying circuitry to control the voltage need to be installed between the sensor receiver, i.e. the antenna, and the heating element. Therefore this embodiment advantageously reduces the number of components mounted in the sensor, which obviously reduces the sensor's manufacturing costs. In addition to that, this embodiment advantageously enables miniaturization of the sensor. Namely, miniaturized rectifiers and miniaturized accompanying circuitries that are currently available, would not be capable of handling the level of power typically required for powering the heating element comprised in the sensor. Furthermore, this embodiment is advantageous in the sense that it prevents an introduction of heating at locations other than the heating element. Namely, the aforementioned rectifier would be heated due to its electrical resistance. This advantageous quality not only increases an accuracy of the sensor, it also increases a sensor's efficiency.

In a further preferred embodiment of the sensor according to the invention, the sensor is situated in or at a wall of the flow path. This embodiment has the advantage that an accuracy of the output signal and/or the further measurement signal generated by the transducer arrangement is increased. Namely, through embedding the sensor in the wall of the flow path, the sensor can be installed in a relatively close proximity of the liquid flowing through the flow path. Consequently, a thermal resistance between the liquid and the sensor is minimized, which reduced thermal resistance is beneficial in terms of reducing a length of time in which a change of the liquid's temperature is detectable by the sensor. This embodiment has further the advantage that the sensor does not physically contact the liquid. The latter quality is essential for medical applications such as intravenous infusion or urinary catheter flow control. Namely, in these applications it is utterly important to prevent the emergency situation in which the sensor or its parts are released and are subsequently being carried towards the human or animal body by the liquid flow.

In a further preferred embodiment of the sensor according to the invention, the sensor is arranged substantially co-axially with the flow path. In this text, co-axially is to be interpreted as an arrangement of bodies or surfaces sharing a common axis in an axial direction. Hence, circular as well as non circular bodies and surfaces allow for a co-axial arrangement. This embodiment has the advantage that the accuracy of the output signal and/or the further measurement signal generated by the transducer arrangement is increased.

It is a further object of the invention to provide a control unit for cooperation with the sensor according to the invention. This object is achieved by the control unit according to the invention, which control unit is characterized by a control transmitter for transmitting the electromagnetic radiation to the sensor receiver. By comprising the control transmitter, the control unit is capable of supplying the electromagnetic radiation for powering the heating element. As a result, the cooperation between the sensor and the control unit may be realized without a physical connection.

In a preferred embodiment of the control unit according to the invention, the control unit comprises a facility for detachably connecting the control unit to the flow path. This embodiment has the advantage that the control unit and the sensor can effectively cooperate while guaranteeing the disposability of the sensor itself and the flow path in which the sensor is preferably embedded. Namely, by detachably connecting the control unit to the flow path, the sensor and the control unit are installable in close proximity of one another for enhancing the transmission of electromagnetic radiation to the sensor receiver, without impeding the disposability of the sensor or a composition of the sensor and the flow path in which the sensor is preferably embedded. Namely, by detachably connecting the channel and the control unit, the channel allows for easy disposition whereas the control unit can be reused. This quality is of particular benefit for medical applications wherein the flow path comprising the sensor is regularly replaced, typically once a day. Furthermore, owing to the preferably wireless supply of power to the heating element via electromagnetic radiation by way of the control transmitter, the disconnecting of the flow path comprising the sensor with respect to the control unit is largely facilitated.

In a preferred embodiment of the control unit according to the invention, the control unit comprises an alarm actuator for generating an alarm signal in response to the output signal generated by the comparator arrangement. This embodiment has the advantage that appropriate action can be employed in case bubbles in gas phase present in the liquid are being detected by the sensor. The alarm signal generated by the alarm actuator may be either audible or visible for the medical professional, or may be embedded by a combination of audible and visible phenomena.

In a preferred embodiment of the control unit according to the invention, the control unit comprises an interrupt actuator for interrupting the liquid from flowing through the flow path in response to the output signal generated by the comparator arrangement. This embodiment has the advantage that e.g. the intravenous supply of medication is automatically interrupted, i.e. the liquid flow is interruptable without the supervision of a medical professional. The latter feature largely enhances a safety of the patient being supplied with medication in for example an intravenous way. Namely, in case the sensor has observed a critical amount of e.g. air present in the liquid flowing through the flow path, an immediate shut down of the liquid supply to the patient is required.

In a preferred embodiment of the control unit according to the invention, the control unit comprises a control actuator for controlling the flow velocity of the liquid flowing through the flow path. This embodiment has the advantage that the velocity at which the liquid is flowing through the flow path is independent from external circumstances such as gravity. The latter quality effectively increases the ease of use for e.g. an intravenous supply system; said system may be employed largely independent from the continuous supervision of a medical professional through employing this embodiment of the control unit according to the invention. Preferably, the control actuator is controllable by a signal relating to a deviation between the predefined flow velocity of the liquid flowing through the flow path and the further measurement signal generated by the transducer arrangement comprised in the sensor. The latter feature has the advantage that no intervention of e.g. a doctor or a paramedic is required to adjust a setting of the control actuator in order to bring the liquid flow velocity in conformity with a predefined medication regime.

A further object of the invention is to provide a system comprising the sensor according to the invention and the control unit according to the invention.

DETAILED DESCRIPTION OF THE EMBODIMENTS

Figure 1:
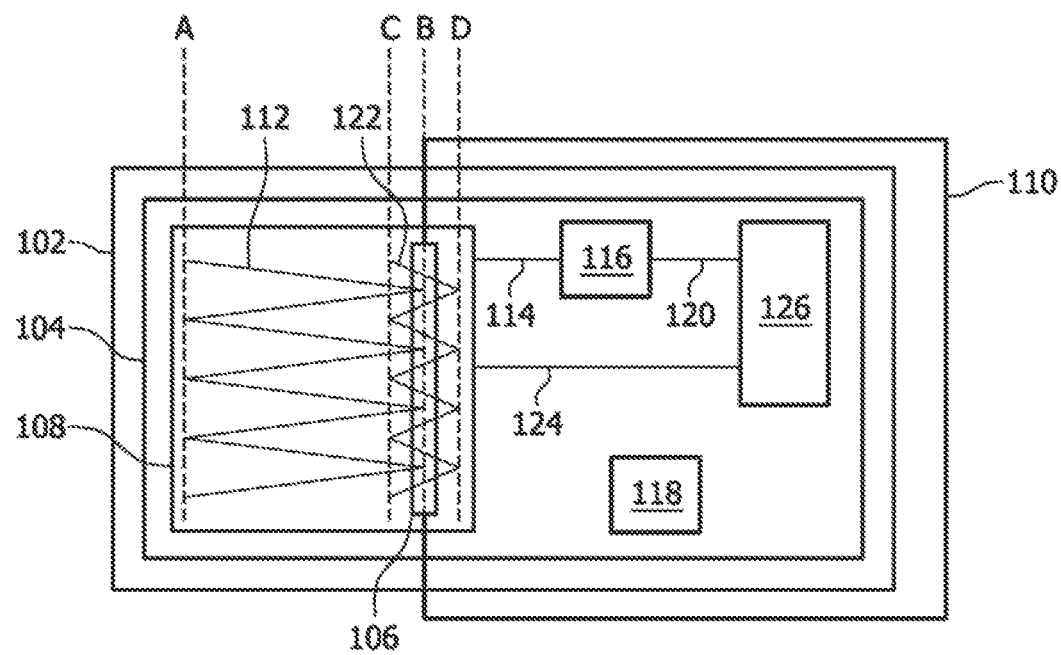
FIG. 1 schematically displays a first embodiment of the sensor according to the invention, wherein the sensor comprises a transducer arrangement build up of two thermopiles.

FIG. 1 displays a sensor 102 comprising a chip 104 which has a substrate manufactured from e.g. poly-imide materials known per se. The benefit of the latter materials is in their relatively low RF power loss. Here RF refers to Radio Frequency, which implies a frequency ranging from approximately 1 MHz up to about 10 GHz. The sensor 102 further comprises an antenna 110 for receiving an electromagnetic radiation. The energy contained in the electromagnetic radiation is employed for powering a heating element 106, which heating element 106 is arranged for heating a liquid, which liquid is flowing along the heating element 106. A level of power provided to the heating element 106 has a predetermined level at least during detection of a possible presence of bubbles in gas phase in the liquid. The heating element 106 is integrated with the antenna 110 through locally providing a relatively large electrical resistance to the antenna 110. Said relatively large electrical resistance is brought about by locally providing a material having a higher electrical resistance, or alternatively, through locally providing a smaller cross-sectional area. Consequently, power will be dissipated along the relatively large electrical resistance, which dissipation will result in heating.

The chip 104 comprises a transducer arrangement 108, which transducer arrangement 108 comprises a first thermopile 112 and a second thermopile 114. In this text, a thermopile refers to a series connection of a plurality of thermocouples. A thermopile produces an output relating to a local temperature gradient or temperature difference rather than measuring an absolute temperature. The first thermopile 112 registers the difference between the temperatures at line A and at line B. Hence, the first thermopile 112 measures the difference between the temperature of the heating element 106 and the temperature at a remote reference position upstream from the heating element 106, which temperature is further referred to as the reference temperature.

Based on an output of the first thermopile 112, the transducer arrangement 108 generates a measurement signal 114 representing a measurement value, which measurement value 114 is indicative for a temperature of the heating element 106. A comparator arrangement 116 is arranged for comparing the measurement value of the measurement signal 114 with a predefined threshold level, and for monitoring a duration of the time during which the measurement value represented by the measurement signal 114 exceeds the predetermined threshold level. Said predetermined threshold level corresponds to a reference temperature attainable by the heating element 106 in response to the predetermined level of power, and to a minimum velocity attainable by the liquid flowing through the flow path. Herein, the liquid flows from line A to line D, along a direction perpendicular to line A. established is directed from line A to line B. The predetermined threshold level may be established experimentally for the liquid at hand, and its value may be stored in the memory 118 comprised in the sensor 102. The comparator arrangement 116 generates an output signal 120. The output signal 120 is indicative for a length of time during which the measurement signal 114 is exceeding the predetermined threshold level. As a result, the output signal 120 is indicative for the amount of bubbles in gas phase that have crossed the heating element 106.

The second thermopile 122 measures the difference between the temperatures at line C and at line D. Therefore, the second thermopile 122 measures the difference between the temperature of the liquid after passing the heating element 106 and the temperature of the liquid prior to passing the heating element 106. Based on a ratio of the output generated by the first thermopile 112 and an output generated by the second thermopile 122, the transducer arrangement 108 generates a further measurement signal 124, which further measurement signal 124 is indicative for a velocity of the liquid.

The sensor 102 further comprises a sensor transmitter 126 for transmitting the output signal 120 and the further measurement signal 124. The employment of the sensor 102 in cooperation with a flow path is disclosed in FIG. 2, which figure relates to the second embodiment of the sensor according to the invention.

Figure 2:
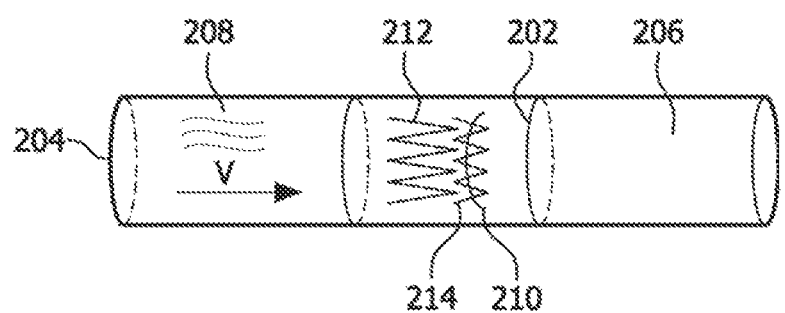
FIG. 2 schematically depicts a second embodiment of the sensor according to the invention, wherein the sensor is situated in the wall of a channel.
Figure 3:
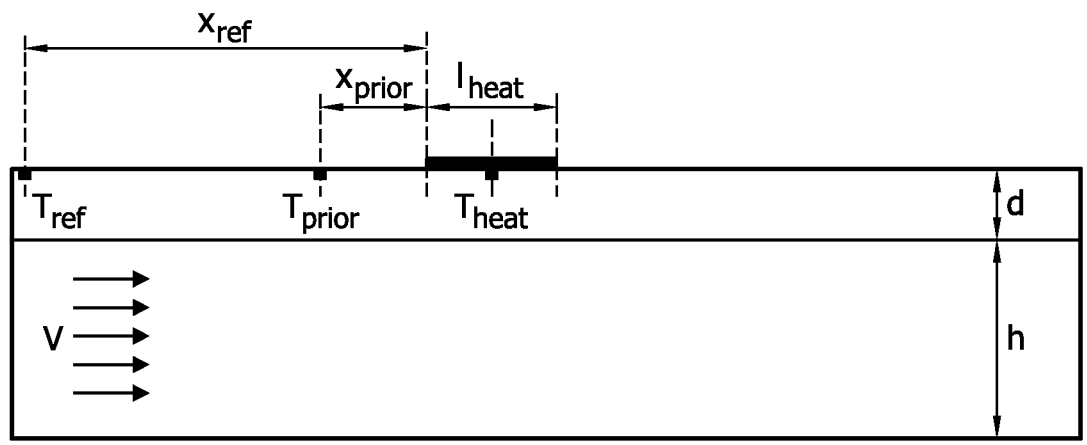
FIG. 3 schematically provides an explanation for the quantities measurable by the transducer arrangement comprised in the first embodiment of the sensor according to the invention.

FIG. 2 displays an embodiment of the sensor according to the invention wherein the sensor 202 is situated at a wall or a wall portion 204 of a channel 206 for measuring a velocity v [m/s] of a liquid 208 flowing through the channel 206. Herein, the liquid 208 is a liquid common in medical applications, such as a water solvable medication or a nutrition in liquid phase. A heating element 210 is arranged for heating the liquid 208. A power source (not shown) comprised in the sensor, e.g. a miniaturized battery, provides a predetermined level of power to the heating element 210. A first thermopile 212 is arranged for measuring the difference between the temperature $T_{heat}$ [K] of the heating element 210 and a reference temperature $T_{ref}$ [K] which is registered at a remote downstream position at a distance $x_{ref}$ from the heating element 210, see also FIG. 4. Based on the output of the first thermopile 212, i.e. $T_{heat}-T_{ref}$, a transducer arrangement (not shown) comprised in the sensor generates a measurement signal indicative for a temperature of the heating element 210. A comparator arrangement (not shown) comprised in the sensor is arranged for comparing the measurement signal with a predefined threshold level, and for monitoring a duration of the time during which the measurement signal 114 exceeds the predetermined threshold level. Said predetermined threshold level corresponds to a reference temperature attainable by the heating element 210 in response to a predetermined level of power, and to a minimum velocity attainable by the liquid in the channel 206. The comparator arrangement generates an output signal which is indicative for a conceivable exceeding of the predetermined threshold level by the measurement signal. As a result, the output signal 120 is indicative for the possible presence of bubbles in gas phase in the liquid 208.

Figure 4:
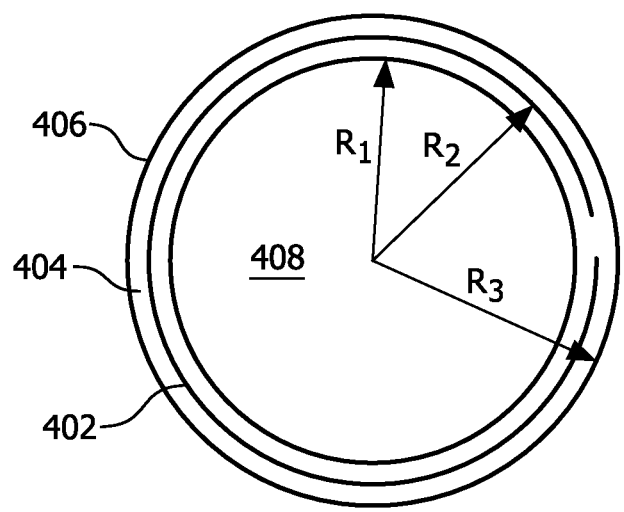
FIG. 4 schematically shows a cross-sectional view of a third embodiment of the sensor according to the invention, wherein the sensor is aligned co-axially with the channel.

Furthermore, the output of the first thermopile 212 relates to the power P [W] supplied to the heating element 210 and the flow velocity v of the liquid 208 in the channel 206 according to the following relationship:

$$T_{heat}-T_{ref}=T_0 \cdot (1-e^{-\alpha 1 x_{ref}}) \qquad [I],$$

wherein:

$$T_0 = \frac{P}{\lambda_{fl} b_{heat} \left( \frac{l_{heat}}{h} + \sqrt{\frac{v^2 h^2}{4 a_{fl}} + 4\kappa} \right)}, \qquad [II]$$

$$\alpha_1 = \frac{v + \sqrt{v^2 + 16 a_{fl}^2 \kappa / h^2}}{4 a_{fl} \kappa}, \qquad [III]$$

$$\kappa = \frac{1}{2} + \frac{\lambda_{wall} d}{\lambda_{fl} h} \qquad [IV]$$

and wherein $l_{heat}$ denotes the length of the heater, d is the distance from the sensor 202 to the liquid 208 and h is the height of the flow channel, see FIG. 4 wherein a graphical explanation is given for the aforementioned quantities. Further, $b_{heat}$ is the width of the heating element 210, $a_{fl}$ is the thermal diffusivity of the liquid 208, $\lambda_{fl}$ is the thermal conductivity of the liquid 208 and $\lambda_{wall}$ is the thermal conductivity of the wall 204, i.e. the thermal conductivity of the material in between the sensor 202 and the liquid 208.

A second thermopile 214 is arranged for measuring the difference between the temperature $T_{after}$ of the liquid 208 after passing the heating element 210 and the temperature $T_{prior}$ [K] of the liquid 208 prior to passing the heating element 210. The output of the second thermopile 214, i.e. $T_{after}-T_{prior}$, relates to the velocity v of the liquid 208 in the channel 206 and the temperature $T_0$, according to the following relationship:

$$T_{after}-T_{prior}=T_0 \cdot (e^{\alpha 2 x_{prior}}-e^{-\alpha 1 x_{after}}) \qquad [V],$$

wherein $$\alpha_2 = \frac{v - \sqrt{v^2 + 16 a_{fl}^2 \kappa / h^2}}{4 a_{fl} \kappa}, \qquad [VI]$$

and wherein $x_{prior}$ and $x_{after}$ respectively denote the downstream distance and the upstream distance from the heating element 110 to the locations at which $T_{prior}$ and $T_{after}$ are being registered by the second thermopile 214, see FIG. 4.

The further measurement signal generated by the transducer arrangement (not shown) comprised in the sensor 202 is based on the ratio τ of the output of the first thermopile 212 and the output of the second thermopile 214. Provided P≠0, the further measurement signal τ follows from the following dimensionless relationship:

$$\tau = \frac{T_{after}-T_{prior}}{T_{heat}-T_{ref}} = \frac{e^{\alpha 2 x_{after}}-e^{-\alpha 1 x_{prior}}}{1-e^{-\alpha 1 x_{ref}}}, \qquad [VII]$$

wherein $\alpha_1$ and $\alpha_2$ follow from equations [III] and [VI], respectively. As apparent from equation [VII], the ratio τ is independent of the power P provided to the heating element 210. Hence, the further measurement signal is robust regarding the actual predetermined level of power that is being provided to the heating element 210.

Furthermore, the further measurement signal according to relationship [V] is invariant under variations in an ambient temperature. Hence, it has no offset regarding temperature. Furthermore, the further measurement signal is sensitive to a substantially large range of the velocity v of the liquid 208 flowing through the channel 206. As a result, the measurement signal provides a relatively large range in which it is indicative for the velocity v. The sensor 202 is calibrated by measuring the ratio τ for a range of velocities and storing the calibration by means of a look-up table in a memory (not shown) comprised in the sensor 202. On the basis of the calibration, the velocity v can be determined during use by measuring τ and by subsequently employing the look-up table. Alternatively, the velocity v can be computed on the basis of [V] by measuring the ratio τ and by subsequently employing an iterative scheme, e.g. the Newton-Raphson method or the bisection method, which imply the computation of v for which the equation $\tau - (e^{\alpha_2 x_{after}} - e^{-\alpha_1 x_{prior}})/(1 - e^{-\alpha_1 x_{ref}})$ equals zero. An advantage of the latter approach is in the fact that modifications in e.g. liquid properties can be accounted for.

FIG. 4 displays a preferred embodiment wherein the sensor 402 is situated in a wall 404 of the channel 406, for measuring a velocity of the liquid 408 flowing through the channel 406. The wall 404 of the channel 406 is made of a suitable plastic. The channel 406 has an inner radius R1 and an outer radius R3. The sensor 402 is arranged co-axially with the channel 406 at a radius R2 for which it holds that R1<R2≤R3. Preferably, to reduce the thermal resistance between the liquid and the flow sensor with the purpose of increasing a detectability of bubbles in gas phase possibly present in the liquid 408, the distance R2–R1 is relatively small, e.g. at about 60 μm. Clearly, the sensor 402 does not physically contact the liquid 408 flowing through the channel 406. Preferably, the sensor 402 envelops the liquid 408 to a relatively large extend in order to increase an accuracy of the output signal generated by a transducer arrangement (not shown) comprised in the sensor 402.

Figure 5:
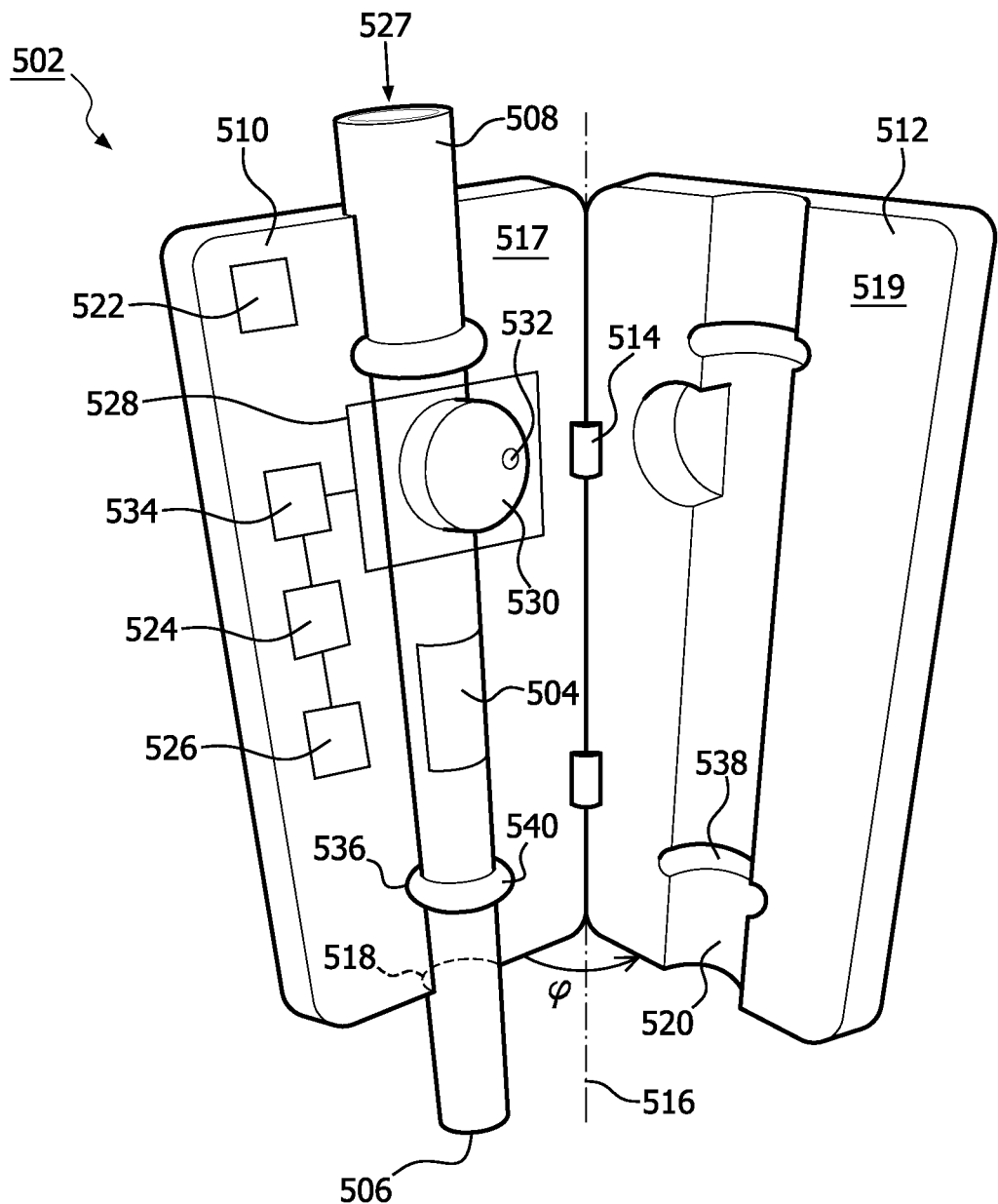
FIG. 5 schematically shows an embodiment of the system according to the invention, wherein the control unit according to the invention is arranged for cooperation with the sensor according to the invention.

FIG. 5 displays an embodiment of the system according to the invention, which system is used in a medical application such as an intravenous infusion system. The system comprises a control unit 502 and a sensor 504. The sensor is situated in a wall 506 of a flow tube 508. The control unit 502 comprises a first body 510 and a second body 512. In this embodiment, both bodies are elongated bodies. In this embodiment, the first body 510 and the second body 512 are connected via a hinge arrangement 514. Hence, the first body 510, the second body 512 and the hinge arrangement 514 constitute a casing. Alternatively, the first and the second body may be connectable by means of screws, snap fasteners or clamps. The hinge arrangement 514 establishes a mutual rotational degree of freedom φ along an axis of rotation 516 for the first body 510 and the second body 512. The first body 510 comprises a first face 517 having a first cavity 518 whereas the second body comprises a second face 519 having a second cavity 520. In case the mutual rotational degree of freedom φ vanishes, i.e. the faces 517 and 519 meet each other hence the casing is closed, a constitution of the first cavity 518 and the second cavity 520 is capable of encasing the channel 508.

The control unit 502 is arranged for cooperation with the sensor 504. For that purpose, the control unit 502 comprises a control transmitter 522 for transmitting an electromagnetic radiation to the sensor receiver (not shown) comprised in the sensor 504 for providing a predetermined level of power, at least during detecting, to the heating element (not shown) comprised in the sensor 504. Herein, the heating element is powered via an energy contained in the electromagnetic radiation itself. Alternatively, the electromagnetic radiation can be employed to enable the energy storage such as a miniaturized battery (not shown) comprised in the sensor, which miniaturized battery powers the heating element in its turn. For the purpose of cooperation, the control unit 502 furthermore comprises a control receiver 524 for receiving an output signal and a further measurement signal whereas the sensor 502 comprises a sensor transmitter (not shown) for transmitting said signals to the control receiver 524.

The control unit comprises an alarm actuator 526, such as a loudspeaker or a siren, for generating an audible alarm based on the output signal received by the control receiver 524. That is, in case the output signal indicates that a critical amount of bubbles in gas phase present in the liquid 527 has crossed the heating element comprised in the sensor 504, a sound is produced in order to warrant the medical professional. The control unit furthermore comprises an actuator 528, which actuator is implemented by a preferably cylindrical body 530 which is eccentrically rotatable around a pivot 532 by an electromagnetic motor 534. The actuator 528 is arranged for interrupting the flow on the basis of the output signal received by the control receiver 524. That is, in case the output signal indicates that a critical amount of bubbles in gas phase has crossed the heating element comprised in the sensor 504, the flow of the liquid through the flow tube is interrupted in order to prevent a potentially harmful amount of bubbles in gas phase from being supplied to a patient. The actuator 524 is further arranged for controlling the flow velocity of the liquid 527 flowing through the channel 508 on the basis of the further measurement signal received by the control receiver 524, provided that the output signal does not indicate that a critical amount of bubbles in gas phase has been detected by the sensor 502. In the absence of bubbles in gas phase in the liquid 527, the electromagnetic motor 534 is controllable by a signal relating to a deviation between a predefined flow velocity of the liquid 527 in the channel 508 and the velocity indicated by the further measurement signal. Hence no intervention of e.g. a doctor or a paramedic is required to adjust a setting with the purpose of bringing the velocity of the liquid 527 in the channel 508 in conformity with a predefined medication regime.

The first cavity 518 comprises a first plurality of circular hollows 536. The first plurality of circular hollows 536 has a non-parallel orientation compared to the first cavity 518. Likewise, the second cavity 520 comprises a second plurality of circular hollows 538. The second plurality of circular hollows 538 has an orientation matching to the orientation of the first plurality of circular hollows 536. The first plurality of circular hollows 538 and the second plurality of circular hollows 536 are arranged for encasing a plurality of bulges 540 mounted on the channel 508. By appropriately encasing the channel 508 through vanishing of the rotational degree of freedom φ along the axis of mutual rotation 516, and by aligning the plurality of bulges 540 with the first plurality of circular hollows 536 and the second plurality of circular hollows 538, a mutual axial position of the channel 508 and the control unit 502 is established.

While the invention has been illustrated and described in detail in the drawings and in the foregoing description, the illustrations and the description are to be considered illustrative or exemplary and not restrictive. The invention is not limited to the disclosed embodiments. It is noted that the sensor and the control unit according to the invention and all their components can be made by applying processes and materials known per se. In the set of claims and the description the word "comprising" does not exclude other elements and the indefinite article "a" or "an" does not exclude a plurality. Any reference signs in the claims should not be construed as limiting the scope. It is further noted that all possible combinations of features as defined in the set of claims are part of the invention.

The invention claimed is:

1. A sensor comprising:
   a heating element for heating a liquid, which heating element is provided with a predetermined level of power at least during detecting,
   a transducer arrangement arranged for generating a measurement signal representing a measurement value indicative for the temperature of the heating element, and
   a comparator arrangement for comparing the measurement value of the measurement signal with a predetermined threshold level, wherein the predetermined threshold level corresponds to a reference temperature attainable by the heating element in response to said predetermined level of power and to a minimum velocity attainable by the liquid in a flow path, and for generating an output signal when the measurement value of the measurement signal exceeds the predetermined threshold level.

2. The sensor according to claim 1, wherein the transducer arrangement is arranged for generating a further measurement signal representing a further measurement value indicative for the velocity of the liquid flowing through the flow path.

3. The sensor according to claim 2, wherein the output signal is indicative for a duration of the time during which the measurement value of the measurement signal exceeds the predetermined threshold.

4. The sensor according to claim 1, wherein the further measurement value of the further measurement signal is based on a ratio of a first spatial temperature difference and a second spatial temperature difference.

5. The sensor according to claim 1, comprising a sensor receiver arranged for receiving an electromagnetic radiation and for powering the heating element following upon receiving the electromagnetic radiation.

6. The sensor according to claim 5, wherein the sensor receiver is an antenna, wherein the antenna comprises the heating element.

7. A control unit for cooperation with the sensor according to claim 5, wherein the control unit comprises a control transmitter for transmitting the electromagnetic radiation to the sensor receiver.

8. The control unit according to claim 7, wherein the control unit comprises a facility for detachably connecting the control unit to the flow path.

9. The control unit according to claim 7, wherein the control unit comprises an alarm actuator for generating an alarm signal in response to the output signal generated by the comparator arrangement.

10. The control unit according to claim 7, wherein the control unit comprises an interrupt actuator for interrupting the liquid from flowing through the flow path in response to the output signal generated by the comparator arrangement.

11. The control unit according to claim 7, wherein the control unit comprises a control actuator for controlling the flow velocity of the liquid flowing through the flow path.

12. The sensor according to claim 1, comprising a sensor transmitter for transmitting the output signal generated by the comparator arrangement and/or the further measurement signal generated by the transducer arrangement.

13. The sensor according to claim 1, wherein the sensor is situated in or at a wall portion of the flow path.

14. The sensor according to claim 1, wherein the sensor is arranged substantially co-axially with the flow path.

* * * * *